US009364607B2

(12) United States Patent
Aguado et al.

(10) Patent No.: US 9,364,607 B2
(45) Date of Patent: Jun. 14, 2016

(54) INJECTION DEVICE INCLUDING A CONTROLLED-FLOW NEEDLE

(75) Inventors: Roberto Garcia Aguado, Valencia (ES); Jorge Ubeda Pascual, Valencia (ES)

(73) Assignee: IPSUMPRO, S.L. (ES)

( * ) Notice: Subject to any disclaimer, the term of this patent is extended or adjusted under 35 U.S.C. 154(b) by 0 days.

(21) Appl. No.: 14/375,471

(22) PCT Filed: Jan. 30, 2012

(86) PCT No.: PCT/ES2012/070048
§ 371 (c)(1),
(2), (4) Date: Feb. 25, 2015

(87) PCT Pub. No.: WO2013/113948
PCT Pub. Date: Aug. 8, 2013

(65) Prior Publication Data
US 2015/0165116 A1    Jun. 18, 2015

(51) Int. Cl.
| A61M 1/00 | (2006.01) |
| A61M 5/158 | (2006.01) |
| A61M 39/22 | (2006.01) |
| A61M 5/142 | (2006.01) |

(52) U.S. Cl.
CPC ............ *A61M 5/158* (2013.01); *A61M 1/0035* (2014.02); *A61M 5/14228* (2013.01); *A61M 39/22* (2013.01); *A61M 2039/224* (2013.01)

(58) Field of Classification Search
CPC combination set(s) only.
See application file for complete search history.

(56) References Cited

U.S. PATENT DOCUMENTS

| 3,957,082 A | 5/1976 | Fuson et al. |
| 4,269,174 A * | 5/1981 | Adair ............................ 128/842 |
| 5,247,966 A | 9/1993 | Stevens et al. |
| 2005/0027262 A1 | 2/2005 | Appling et al. |
| 2009/0163860 A1 | 6/2009 | Patrick et al. |

FOREIGN PATENT DOCUMENTS

WO    WO02055145    *  7/2002   ............ A61M 19/00

OTHER PUBLICATIONS

English language translation of written opinion and international search report for PCT/ES2012/070048 and publication of PCT/ES2012/070048.

* cited by examiner

*Primary Examiner* — Scott Medway
(74) *Attorney, Agent, or Firm* — Garcia-Zamor IP Law; Ruy M. Garcia-Zamor (57) ABSTRACT

Controlled-flow needle injection device comprising a needle or cannula (1) with standard coating for performing nerve blocks; a first independent line for administering local anaesthetic (4) connected to a high-pressure syringe; and a second independent aspiration line (5) connected to a mechanical aspiration syringe; characterized in that it comprises a manual flow control element (10) having a first aspiration position (11) that enables the connection between the needle or cannula (1) and the aspiration line (5); a second administration position (12) that enables the connection between the first independent administration line (4) and the needle or cannula (1); and a third neutral position (13) without administration or aspiration; and wherein by sliding it switches from a neutral position (13) to an aspiration position (11) and from there to an administration position (12) by means of continuous pressure exerted by the anesthesiologist, returning to the aspiration position (11) when said pressure is no longer exerted towards the administration position (12); and wherein the pressure exerted on the flow controller (10) is exerted only by the anesthesiologist's dominant hand.

7 Claims, 8 Drawing Sheets

INJECTION DEVICE INCLUDING A CONTROLLED-FLOW NEEDLE

OBJECT OF THE INVENTION

The object of the invention is a needle/cannula which allows control of fluid flow therethrough and in the direction thereof enabling, among other applications, the performance of nerve blocks through the administration of local anaesthetics (LA) without need for an assistant, whether using neurostimulation or ultrasound as the nerve location or identification method.

BACKGROUND OF THE INVENTION

The performance of regional anaesthesia is a first-line anaesthesia option. The object of any regional blocking technique is to deposit the sufficient volume and concentration of the local anaesthetic as close as possible to the nerves to be blocked. Blocking of peripheral or plexus nerves is used in surgical anaesthesia and to provide adequate postoperative analgesia to the patient with minimum side effects, as well as in the treatment of various chronological pathologies.

The regional techniques known in the current state of the art are based on surface anatomy landmarks, i.e. on "blind" methods for locating nerve structures, aided by the appearance of "clicks", parasthesias, etc. At present, through advances in technology, more precise techniques such as neurostimulation and ultrasonography are applied, representing a current nerve location and identification alternative which has displaced classical techniques.

In general, the election of a certain nerve location technique will depend on personal preference, the anaesthesiologist's experience and the possibilities of the environment in which it is performed and of the patients themselves.

The use of a peripheral nerve stimulator or neurostimulator is a current nerve location and identification alternative which has displaced other direct classical techniques, such as parasthesias, and indirect techniques, such as "clicks". This method aims to locate the motor component of one or several peripheral nerves through the administration of a continuous current, that stimulates the nerve by means of a Teflon-coated needle, which acts as a coating of the needle cylinder that prevents dispersion of the electric current, connected to an anode (negative), the frequency (in Hz), current (in mA) and duration (in msec) of which, according to the device, are controlled by the operator. The nerve to be stimulated remains interposed between the needle and the electrode. It is a highly widespread technique that necessarily requires the presence of an assistant for execution thereof. When the needle approximates the nerve, muscular responses are produced that the anaesthesiologist must be aware of for that block in particular, consequently performing injection of LA with the assistant's aid.

The use of ultrasound to perform regional blocks has dramatically changed this situation, reaching an increasingly ideal situation in the practice of nerve blocks. Now, not only is it possible to directly view the nerve structure to be blocked in order to deposit anaesthesia in the periphery thereof, but it is also possible to locate the adjacent structures to prevent complications such as vascular punctions or pneumothorax and, even more importantly, the distribution of the local anaesthetic around these nerve structures can be observed in real time and can be modified by repositioning the needle to achieve enhanced nerve block.

The technical problem raised in this solution arises from the real location and anatomic integration in the patient of the image shown on the ultrasound screen, the need to be familiarised with ultrasound systems and for in-depth knowledge of the underlying anatomy.

It is standard practice, during the performance of nerve block, for the anaesthesiologist to use both hands (ultrasound probe and needle), the dominant hand being that holding the needle. Once the place to deposit the LA has been chosen, the anaesthesiologist has the imperative need for an assistant or collaborator. The collaboration of an assistant who follows the anaesthesiologist's instructions with respect to the suction through a line connected to the needle and/or administration of small volumes of LA is required. This process, in addition to requiring close collaboration, is repeated throughout the performance of the technique and discrepancies and errors often occur in the administration of the local anaesthetic in terms of exact location, distribution and desired volumes.

The dynamism and flexibility of the ultrasound enables the nerve path to be traced from its origin to the distal ends thereof. This allows the plexuses and nerves to be located and blocked in any point along their path, adapting to each specific situation and personalising the technique for each specific patient.

Therefore, ultrasound offers a significant number of advantages that convert it into the perfect technique for application in regional anaesthesia, as:

A direct view of the structures is obtained.

The distribution of the local anaesthetic around the nerve is observed in real time.

The total doses of the drug (local anaesthetic) are optimised.

Safety is increased.

The aforementioned indications advised against are obviated.

It can be combined with other techniques such as neurostimulation.

The technical problem of this technique is that during the performance of the nerve block the anaesthesiologist uses both hands, although this problem has been addressed through the use of drug pumps operated by the anaesthesiologist, this system has not become widespread and continues to be an unsolved problem.

Therefore, a system that facilities or enhances the performance of the technique, improving its synchronisation and the administration of LA, is required.

DESCRIPTION OF THE INVENTION

The object of the controlled-flow needle is to facilitate the performance of nerve blocks through the administration of local anaesthetics without the aid of an assistant.

The controlled-flow needle essentially includes a manual flow controller in the needle connector which allows both the administration of the local anaesthetic and negative suction by means of two independent lines in the needle itself, controlled by the anaesthesiologist using the hand that performs the puncture.

In general, the needle is supplied in the form of a set or kit comprising said needle, the suction and/or administration controller, a line for administering local anaesthetic, a suction line, a vacuum syringe, a 20 ml pressurised injection syringe, with or without LA, and an inner lining for housing catheters.

The needle advocated by the present invention facilitates and enhances the performance of nerve blocks, with total synchronisation between the progress of the needle and the moment in which the LA is administered, as it is all performed by the same person, thereby adapting the distribution around the nerve to be blocked and reducing complications.

Likewise, this also favours greater efficiency and dynamism in the performance of local and regional techniques.

Given that most of the nerves blocked are surrounded by important blood vessels which are anatomically proximate to vital organs, complications during nerve blocks may be vascular, respiratory and neurological. These risks are minimised by adequate nerve location, adequate dosage of LA and successive suctions. Suction must be performed before depositing a volume of local anaesthetic in any area as it considerably reduces the possibility of intravascular injection. The purpose of the suction is to determine whether the needle tip rests inside a blood vessel. Suction requires the generation of negative pressure that is transferred to the needle tip. Any trace of blood constitutes positive suction, in which case the LA must not be deposited. The needle object of the invention has a suction line which allows suction to be controlled by the anaesthesiologist performing the block, thereby providing a safety measure for the patient aimed at preventing possible complications, as well as a means for adapting the volume of LA injected by the administration line.

Therefore, the needle object of the present patent, on including a structural element that manually controls the administration of LA by the anaesthesiologist in a standard nerve block needle, improves nerve block efficiency, facilitating execution thereof and involving a safer technique, i.e. with less possibility of errors.

The use of the needle object of the invention could become a new actuation standard, improving the resources used, i.e. with greater efficiency. Likewise, this device could have other applications in different areas whenever someone must suction/inject a substance through a needle and requires the aid of another person, as said aid is not required. In general, the greatest advantage of the invention is independence with respect to an assistant.

The device described is essentially manual, although there is a possibility of adaptations to electronic systems or mechanical modifications, always aimed at controlling flow through a needle. In this regard, the possibility of taking samples (suction) using the same needle could be used in substance infusion systems in accordance with their plasmatic concentrations (open-loop TCI or maintenance of blood glucose levels, currently under development) or any type of medical suction and irrigation application, for example, in ophthalmological applications.

A new field of application is opened, for example in ophthalmology, where a surgeon inserts a coaxial phacoemulsification probe, which consists of a hollow cylindrical tip surrounded by an irrigation hose, in such a manner that it remains as a tube (suction) in the interior of another tube (irrigation). Phacoemulsification systems normally regulate the control panel disposed at the front of the equipment and the programmed system functions are controlled by means of a pedal. The device object of this patent could enable the implementation of manually governed phacoemulsification systems. Logically, the precision and rigour of the operator's hand would be superior to those of his/her foot, which could lead to the substitution of pedals.

Throughout the description and claims, the word "comprises" and its variants does not aim to exclude other technical characteristics, additives, components or steps. For persons skilled in the art, other objects, advantages and characteristics of the invention shall be inferred partially by the description and partially from the practice of the invention. The following examples and drawings have been provided for illustrative and non-limiting purposes. The present invention also covers all the possible combinations of the particular and preferred embodiments indicated herein.

BRIEF DESCRIPTION OF THE DRAWINGS

Following is a brief description of a series of drawings that help to better understand the invention and which are expressly related to an embodiment of said invention, presented as a non-limiting example thereof.

FIG. 3 shows the syringes with mechanical-type (spring) positive suction and pressure system. The line connected to the syringe is shown, displaying the effect of the suction (FIG. 3A) and its loss (FIG. 3B).

FIG. 4 shows the syringes with "vacutainer"® type positive suction and pressure system. (FIGS. 4A and 4B).

FIG. 5 shows an internal diagram of the controller (FIG. 5A) showing the controller sliding in the direction of the needle axis; and where

FIG. 6 shows an internal diagram of the controller (FIG. 6A) showing the controller sliding transversely to the needle axis; and where

PREFERRED EMBODIMENT OF THE INVENTION

The present invention proposes a controlled-flow needle that includes means for controlling fluid flow in the needle which allow, manually and at will by the dominant hand of the anaesthesiologist performing the nerve block, both the timing and volume required during the performance of the technique, obviating the need for a collaborator and thereby increasing the effectiveness, speed and safety of the procedure.

As can be observed in the attached figures, the controlled-flow needle object of the present invention comprises, at least:

A needle or cannula (1) with standard coating for performing nerve blocks, with or without neurostimulation. In a particular embodiment a 21 G calibre needle is preferably used.

An outer sheath (2) over the needle (1) with a flange for sliding it upon administering the local anaesthetic and which also allows the passage of a catheter if necessary.

A cable for electrostimulation (3).

An independent line for administering local anaesthetic (4).

An independent line for suction (5).

A flow controller element (10) which moves from the suction position (11) to the administration position (12). It is indistinct whether the sliding is in the direction of the needle (1) axis or transversely thereto.

A pressurised syringe with or without local anaesthetic (between 5 ml and 20 ml depending on the application).

A mechanical suction syringe, i.e. having a spring in the plunger, or a "vacutainer"® type vacuum syringe.

The flow control element (10) is manual, mechanical and sliding. This controller has three positions: neutral (13), suction (11) and administration (12). The neutral position (13) does not administer or suction, and is constituted at the starting point. The suction position (11) is the position where the independent suction line (5) remains open and is also the position to which the flow controller (10) will return, provided that the fluid administration position (12) does not remain activated.

Figure 1:
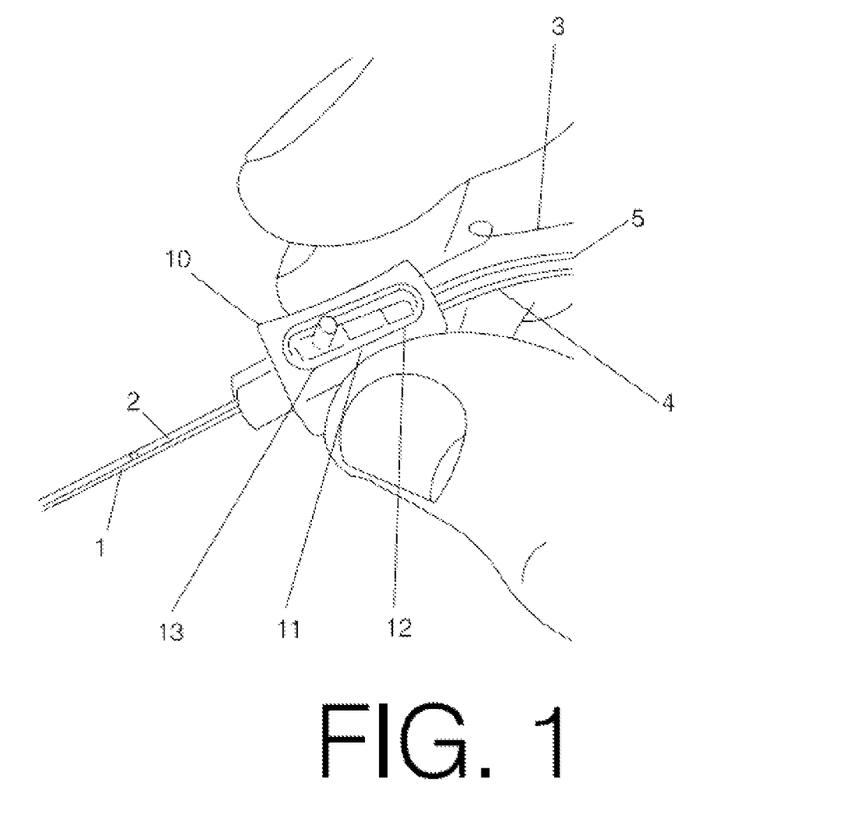
FIG. 1 shows an image of the controlled-flow needle with the three position possibilities: R1: "neutral", R2: Suction; R3: "administration".
Figure 2:
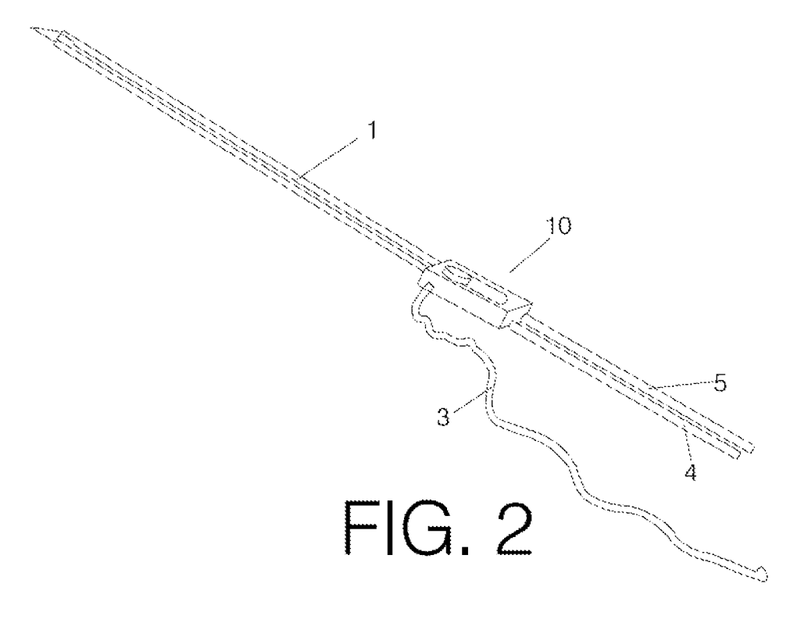
FIG. 2 shows an external diagram of the controller with the slidable pusher.
Figure 3A:
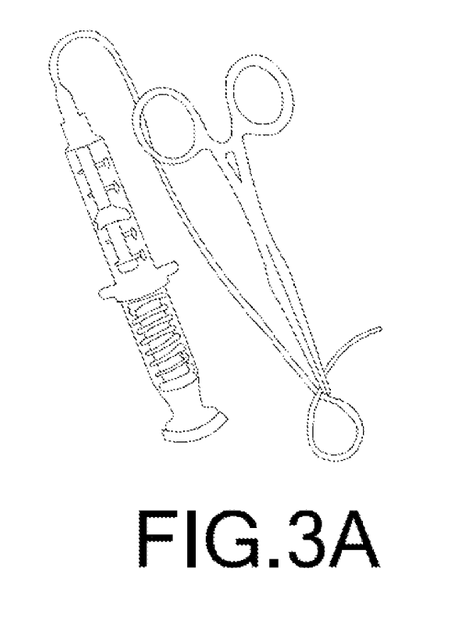
Figure 3B:
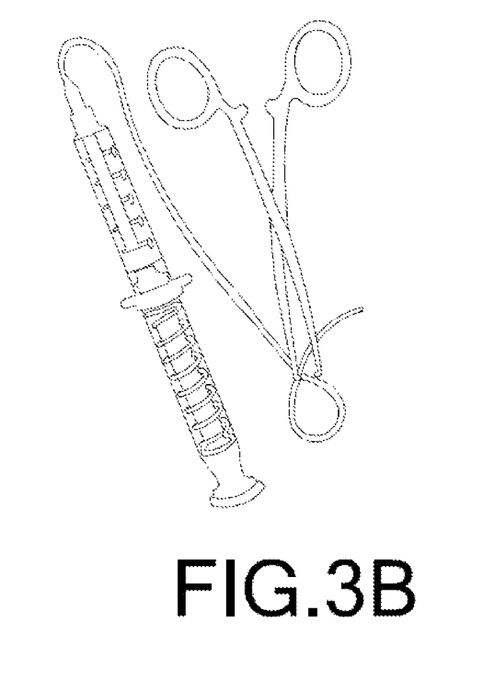
Figure 3C:
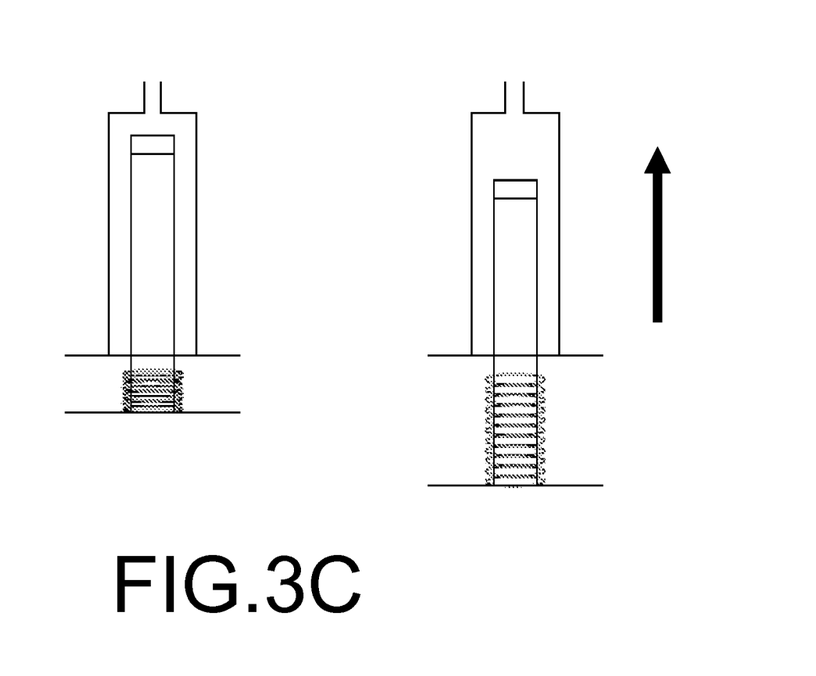
FIG. 3C shows the syringe with the reverse spring for connecting to the administration line (positive pressure).
Figure 4A:
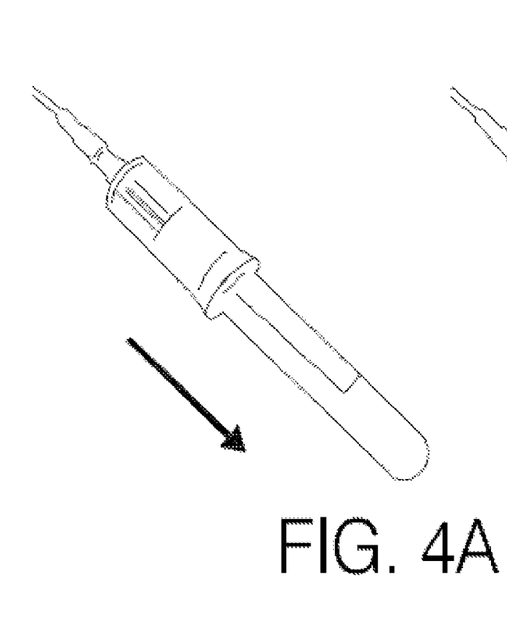
Figure 4B:
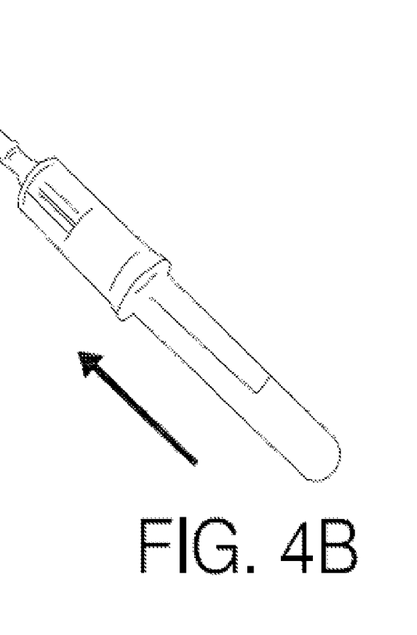
Figure 5A:
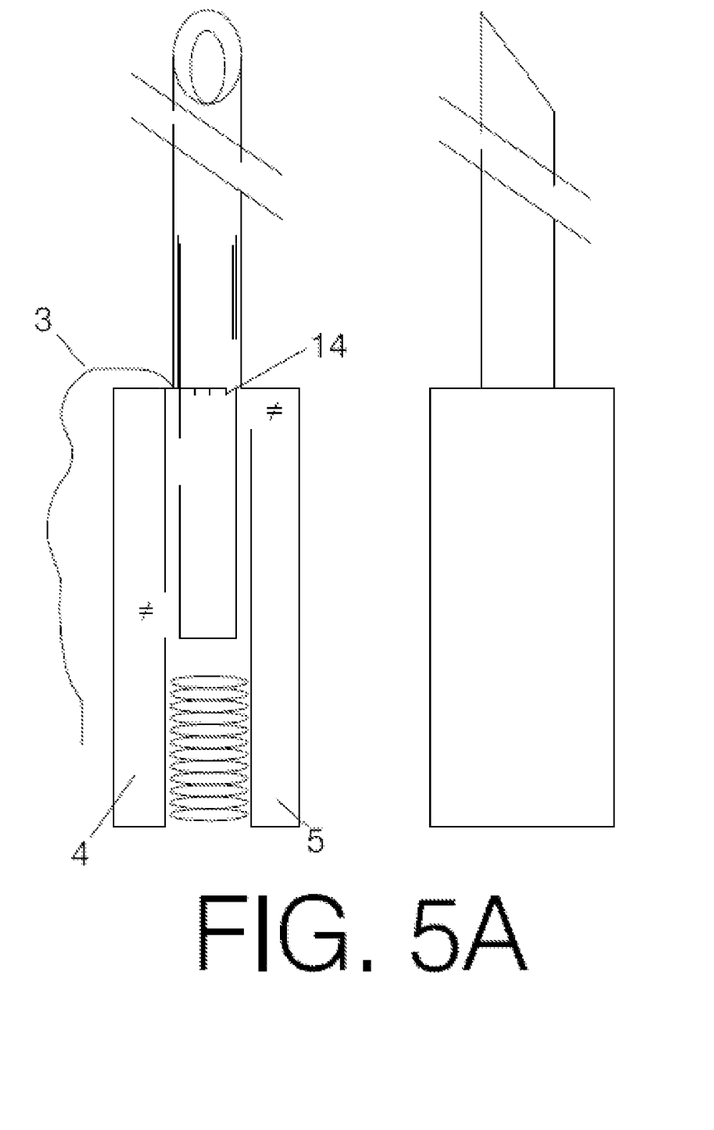
Figure 5B:
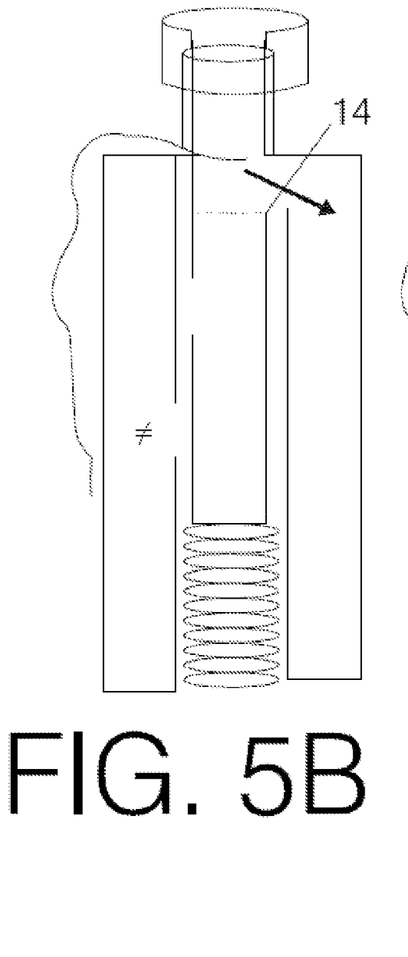
FIGS. 5B and 5C show the controller in the suction and administration positions.
Figure 5C:
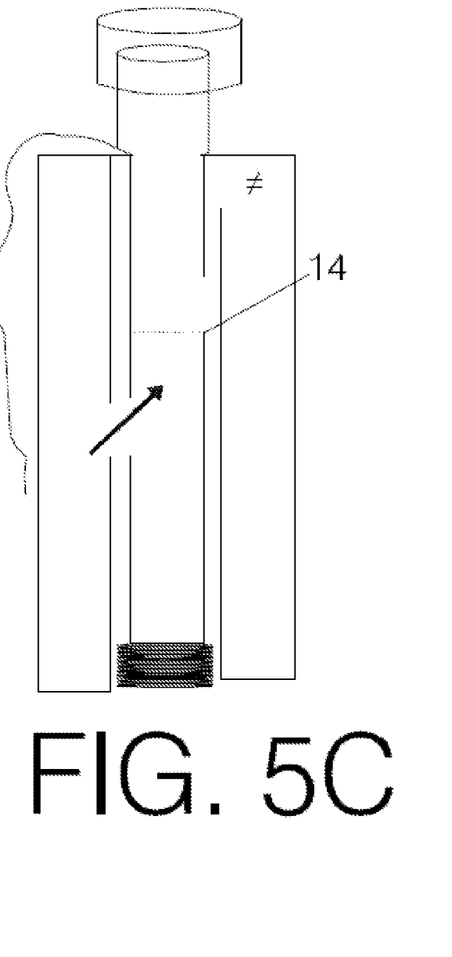

The flow controller (10) comprises two particular embodiments:

Sliding in the direction of the needle, where the controller can be located on one of the sides, preferably in the upper position, to be slid using the index finger. In FIG. 5a, it begins in a neutral position (13) where, after the puncture, the controller is slid towards a first suction position (11), as can be observed in FIG. 5b, in correspondence with the independent suction line (5), position to which the controller will always return provided that the anaesthesiologist does not maintain the second administration position (12) activated, in correspondence with the independent administration line (4), FIG. 5c.

Figure 6A:
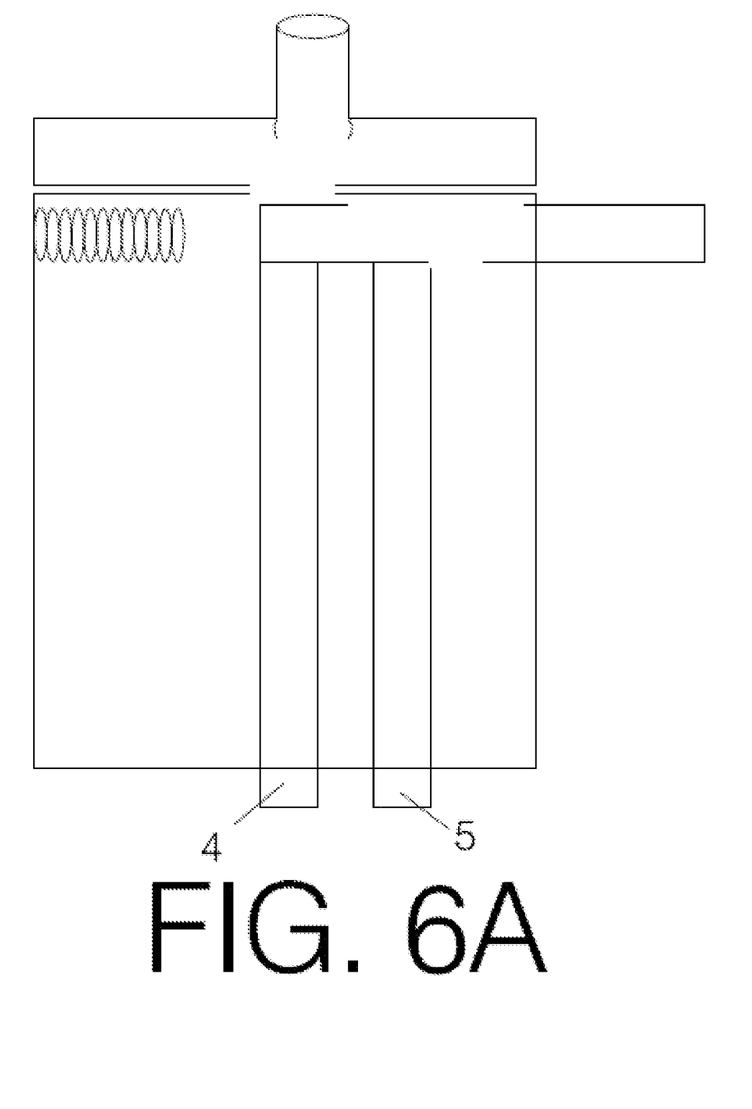
Figure 6B:
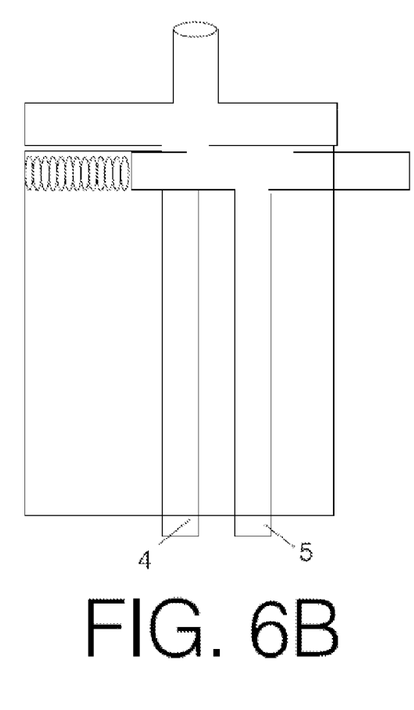
FIGS. 6B and 6C show the controller in the suction and administration positions.
Figure 6C:
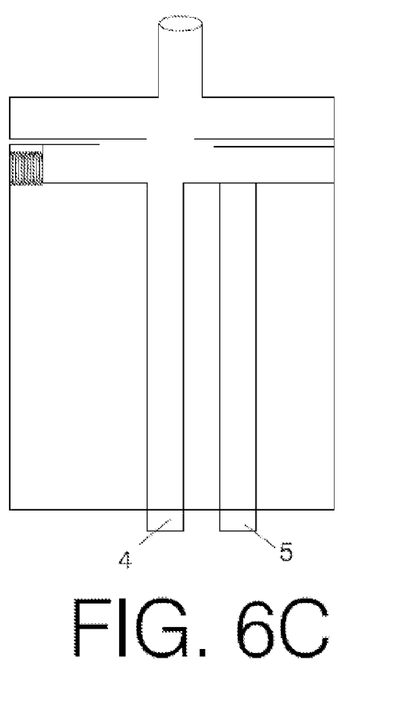

Transverse sliding in the direction of the needle, where the controller can be located on one of the sides to be pressed. As in the previous embodiment, the controller begins in a neutral position (13), FIG. 6a, and after the puncture, the first working position or suction position (11) is slid or pressed in correspondence with the independent suction line (5), FIG. 6b, position to which the controller will always return provided that the anaesthesiologist does not maintain a second administration position (12) activated, in correspondence with the independent administration line (4), FIG. 6c.

In both options, the dotted line represents a resistance (14) that must be overcome from the neutral position (13) before moving to the suction position (11). This resistance (14) is materialised in a ring or protuberance that hampers sliding (option (a)) or pressure (option (b)). Therefore, when the pressure ceases, it will never move to the neutral position unless purposefully actuated, for example at the start of the procedure or priming. The use of the needle object of the present invention begins with a first stage of preparation or priming, performed in the same manner as in the current state of the art. The purpose is to avoid the introduction of air bubbles which, in the case of ultrasound, also hampers the view of the images due to the opacity of the air for the ultrasound waves. Therefore, in a first phase, with the controller element (10) in the neutral position (13), the independent administration line (4) is connected to a pressurised syringe with the system defined and the independent suction line (5) is left open. Subsequently, the controller is moved to the administration position (12) until the local anaesthetic flows out of the needle tip (1). At that moment the administration is suspended and controller returns to the neutral position (13). At that moment, connection can be made to the independent administration line (5) and the device is ready for use.

Once the needle object of the invention has been primed, the anaesthesiologist can, in a self-sufficient manner and without need for an external collaborator, perform the technique correctly and safely. Once the needle punctures the skin, the controller is moved to the first working position, i.e. to the suction position (11), in such a manner that what happens to the needle tip will be under permanent suction conditions. This guarantees that the needle tip (1) is not intravascular, preventing systemic toxicities or damage to any vascular structure during the progress of the needle (1). This implies an improvement in whatever technique is used to detect the nerve in question during this phase.

Once the nerve to be blocked has been located, whether via neurostimulation and/or ultrasound, the anaesthesiologist, using the hand that performs the puncture, will proceed to administer or dissect the tissues with the local anaesthetic, surrounding and thereby adapting the distribution of the anaesthetic around the nerve to be blocked.

The combination of the progress of the needle and the displacement of the tissues by the injection of local anaesthetic is significantly improved by the invention, as it is the anaesthesiologist who controls the time and volume of the anaesthetic he/she administers in a dynamic and synchronised manner, facilitating the positioning of the needle in the exact location and avoiding obstacles by means of careful hydrodissection.

Similarly, it is sufficient to cease the pressure/displacement during administration and the controller will return to the suction position (11) as many times as required, as the vacuum syringe, unless it suctions due to inadvertent vascular puncture, should not lose significant volume as no air is suctioned in the tissues.

The level of sensitivity is also better than if performed using a pedal-type system or with an assistant, as the controller element (10) is held in the anaesthesiologist's dominant hand and index finger thereof, on the same progressing needle (1).

Lastly, the response time, which is also important, is immediate in the invention with respect to other remotely controlled drug pumps, as the length of the line mitigates the response to changes in pressure and the volume administered is modified.

Although the device described is essentially manual, it is evident to a person skilled in the art that an obvious evolution of the invention would be the remote control thereof. This would be carried out on the basis of the concept advocated in the present invention wherethrough it is controlled by the anaesthesiologist's hand, but using a remote control. Therefore, using a wireless system and the same three positions as the described controller, fluid suction or administration commands would be sent to a peristaltic pump.

The invention claimed is:

1. Injection device comprising:
   a needle or cannula with standard coating for performing nerve blocks;
   a first independent line for administering local anaesthetic
   a second independent aspiration line; and
   at least one high-pressure syringe and a mechanical aspiration syringe; said controlled-flow needle also comprises a manual flow control element which by sliding it switches from a neutral position to an aspiration position and from there to an administration position, wherein the manual flow control element is only maintained in the administration position while a continuous pressure is applied to and maintained on the manual flow control element such that if the continuous pressure on the manual flow control element is not maintained the manual flow control element returns to the aspiration position; and wherein said aspiration position enables the connection between the second independent aspiration line and the needle, while the administration position enables the connection between the first independent administration line and the needle or cannula,
   wherein a portion of a conduit is located within the manual flow control element and is configured to move when the manual flow control element switches from the neutral position to the aspiration position and from the aspiration position to the administration position,
   and wherein the first independent line and the second independent aspiration line each have a first line portion and a second line portion, respectively, that is located within the manual flow control element and located adjacent to the portion of the conduit.

2. The injection device according to claim 1, wherein the needle or cannula is equipped with an outer sleeve having a flange configured to be slid upon administering the local anaesthetic and where through a catheter can pass through said outer sleeve.

3. The injection device according to claim 1, which also comprises an electro-stimulation cable.

4. The injection device according to claim 1, wherein the control element is a remote control connected electrically or wirelessly to a peristaltic/vVenturi pump that would regulate the switching between the neutral, aspiration; administration work positions.

5. The injection device according to claim 1, wherein when switching from the neutral position to the aspiration position and the aspiration position to the administration position, the injection device does not electronically communicate with any other device.

6. The injection device according to claim 1, wherein the continuous pressure applied to the manual flow control element to maintain the manual flow control element in the administration position is in a direction away from the aspiration position, and wherein a spring returns the manual flow control element to the aspiration position if the continuous pressure away from the aspiration position is not maintained.

7. The injection device according to claim 1, wherein the portion of the conduit has at least one opening thereon and the first line portion and the second line portion each have an opening thereon, wherein when the manual flow control element is moved to the aspiration position, the manual flow control element manually moves the portion of the conduit such that the opening on the second independent aspiration line is aligned with one of the at least one openings on the portion of the conduit, and wherein when the manual flow control element is moved to the administration position, the manual flow control element manually moves the portion of the conduit such that the opening on the first independent line is aligned with one of the at least one openings on the portion of the conduit.

* * * * *